United States Patent [19]

Feucht

[11] Patent Number: 5,067,953
[45] Date of Patent: Nov. 26, 1991

[54] CIRCUIT FOR CONTROLLING AN ELECTRO-THERAPY DEVICE

[75] Inventor: Peter Feucht, Berlin, Fed. Rep. of Germany

[73] Assignee: Siemens Aktiengesellschaft, Berlin and Munich, Fed. Rep. of Germany

[21] Appl. No.: 522,108

[22] Filed: May 11, 1990

[30] Foreign Application Priority Data

May 19, 1989 [EP] European Pat. Off. ......... 89109074.8

[51] Int. Cl.⁵ .............................................. A61B 17/39
[52] U.S. Cl. ......................................... 606/34; 606/42
[58] Field of Search .............................. 606/34, 37–40, 606/42; 128/800

[56] References Cited

U.S. PATENT DOCUMENTS 4,378,801  4/1983  Oosten ................................. 606/37

FOREIGN PATENT DOCUMENTS 2429021  1/1976  Fed. Rep. of Germany .
2457900  5/1976  Fed. Rep. of Germany .
2457221  6/1976  Fed. Rep. of Germany .

Primary Examiner—Lee S. Cohen
Attorney, Agent, or Firm—Hill, Van Santen, Steadman & Simpson

[57] ABSTRACT

For separating voltage potentials from a handle switch in a circuit for controlling an electro-therapy device, the circuit includes at least one electrode carrying high voltage connected to the switch, with the switch being in series with a rectifier and the series combination being electrically connected to a secondary side of a quadrupole component, which transmits alternating current and blocks direct current. The primary side of the quadrupole component is connected to an alternating current source, the secondary side being voltaically separated from the primary side. Actuation of the switch causes a directionally dependent change in an electrical parameter at the primary side of the quadrupole component. An evaluation unit is connected at the primary side, and is also connected to the electrode. The evaluation unit includes circuitry which is capable of altering the delivery of high voltage (a.c. current) to a patient via the electrode, and undertakes such alteration upon the detection of the directionally dependent change in the electrical parameter at the primary side.

21 Claims, 4 Drawing Sheets

CIRCUIT FOR CONTROLLING AN ELECTRO-THERAPY DEVICE

BACKGROUND OF THE INVENTION

1. Field of the Invention

The present invention is directed to a control circuit for an electro-therapy device, i.e. a device for administering medical treatment to a patient in the form of electrical energy, such as an RF surgery device, and in particular to such an electro-therapy device having at least one electrode carrying a high voltage for delivery to a patient and at least one switch connected to the electrode.

2. Description of Prior Art

In conventional electro-therapy devices, a treatment electrode is structurally combined with at least one switch, for example at or in a handle which is used to manipulate the treatment electrode. The switch gives the user, i.e. the person administering the treatment, the possibility of immediately influencing the operation of the electro-therapy device. In the simplest case, the switch controls an on-off function. For safety reasons, especially to protect the person to be treated from the high voltage of the electrode, the switch is generally physically separated from the source of voltage potential and from the ground for the electro-therapy device. Such electrodes are usually exposed to rugged operating conditions, for example, out of doors when resuscitating cardiac activity with electrical shocks (stimulation currents), or in operating room when manipulating in or at surgical wounds. In any case, the risk is present that moisture, for example rain in the out of doors or body fluid in the operating room, can proceed to the switch at the electrode. Such fluid may create new current paths to the high voltage, or may short circuit existing current paths, which may not only result in a deterioration of the electro-therapy device, but also jeopardizes the safety of the person to be treated.

It is also a desirable feature of such electro-therapy devices that the electrode be easy to manipulate. Usually the electrode will include more than one switch associated therewith. The rugged operating conditions, particularly the actions of moisture, require a high outlay for insulation between the switch and the electrode, given the high voltages which are present at the electrode. If such a handle were constructed, it would be too large and too heavy to easily manipulate. This disadvantage could be avoided, in theory, if the effective insulation between the switch and the high voltage of the electrode were displaced into the electro-therapy device itself (i.e., out of the handle). If this were done, however, a multitude of components which are electrically connected to the switch, for example relays and components for generating the operating voltage, must then be heavily insulated.

A circuit for controlling a RF surgery device is disclosed in German AS 24 57 900. In this known device, a filter tuned to the frequency of a low-frequency auxiliary signal contains a transformer for voltaically separating the potentials. In combination with a resonant capacitor, the primary side of the transformer forms the emitter resistor of a transistor switching stage connected thereto. Under the resonant condition, the filter has a high impedance which causes the switching transistor to be non-conducting. The secondary side of the filter also contains a resonant capacitor, which can be shorted by a switch connected thereto. When the switch is actuated, the resonant condition is no longer present, i.e. the filter is detuned, which causes the impedance at the primary side of the filter to drop, and the switching transistor becomes conductive, as a result of which the RF generator is switched. This control circuit, therefore, requires an additional frequency filter, which must be insulated, for each switch which is provided.

A circuit is disclosed in German OS 24 57 221 for selecting types of current in a RF surgery device which includes an electrode handle having a two-poled switching arrangement with two actuators, so that different current levels can be delivered to a patient by respectively depressing one or both of the actuators. The handle is remote from a housing of the surgery device. A blocking stage disposed in the housing provides the only means for electrically connecting the components of the handle to the components in the housing. The housing also contains a high-frequency current source, a transformer, and control circuitry. The control circuitry and the blocking stage are connected to the secondary of a transformer which supplies a low-frequency a.c. voltage to the control circuitry. The control circuitry includes two relays and two diodes respectively connected in series therewith, the diodes being connected with opposite polarity. Each relay is bridged by a capacitor. The blocking stage permits direct current to pass therethrough, but blocks high-frequency current. The blocking stage is a pentapole consisting of two chokes and three capacitors. Again, a relatively high outlay for electrical insulation is required at these components.

SUMMARY OF THE INVENTION

It is an object of the present invention to provide an electro-therapy device which achieves a separation of the voltage potential between switch means and switched means with reduced insulation outlay, so that a plurality of switches, constituting the switch means, can be connected to a common arrangement for separating potential without significantly impairing the manipulability of the unit in which the switches are disposed.

The above object is achieved in accordance with the principles of the present invention in an electro-therapy device wherein each switch is connected in series with a rectifier, and is electrically connected to a secondary side of a quadrupole element which transmits alternating current and blocks direct current. The quadrupole element has a primary side coupled to an alternating current source. Actuation of the switches causes a directionally dependent reaction in an electrical parameter at the primary side of the quadrupole element. An evaluation and control circuit is connected at the primary side, which detects the occurrence of such a directionally dependent reaction, and is also connected to the component of the apparatus which administers electrical energy to a patient, such as the electrode in a high-frequency surgery device. Upon the detection of a directionally dependent reaction, the evaluation and control circuit appropriately alters the delivery of electrical energy to the patient.

As a consequence of the above arrangement of components, only one insulating component, namely the quadrupole component, is needed between the switches and the switched components. This permits the quadrupole component to be moved away from the components which are exposed to rugged operating conditions, such as moisture and/or splashing water, and disposed in the housing for the electro-therapy device, for example, adjacent the connecting sockets at the housing for the remote, hand-held instrument. As seen by the switches, therefore, high voltage is present only in circuit portions which are "behind" the quadrupole component. In combination with rectifiers, this permits a plurality of switches to be connectable to only a single quadrupole component. If two switches are provided at the hand-held instrument, the switches in combination can assume four states (neither actuated, one or the other actuated, or both actuated) with no additional insulation outlay.

The switches may be interruptable contacts, plugs, (for example, pluggable electrodes with bipolar/-monopolar switching, if the electro-therapy device is a high frequency surgery device), push buttons, slide switches or the like. The quadrupole can be a transformer, or can be realized with capacitors, filters and the like, adapted to the particular application. The directionally dependent reaction which arises at the primary side of the quadrupole given a change in the switching state at the secondary side of the quadrupole may be a voltage and/or current change of a magnitude capable of being detected and evaluated. The rectifiers connected in series with each of the switches may be semiconductor diodes.

DESCRIPTION OF THE PREFERRED EMBODIMENTS

Figure 1:
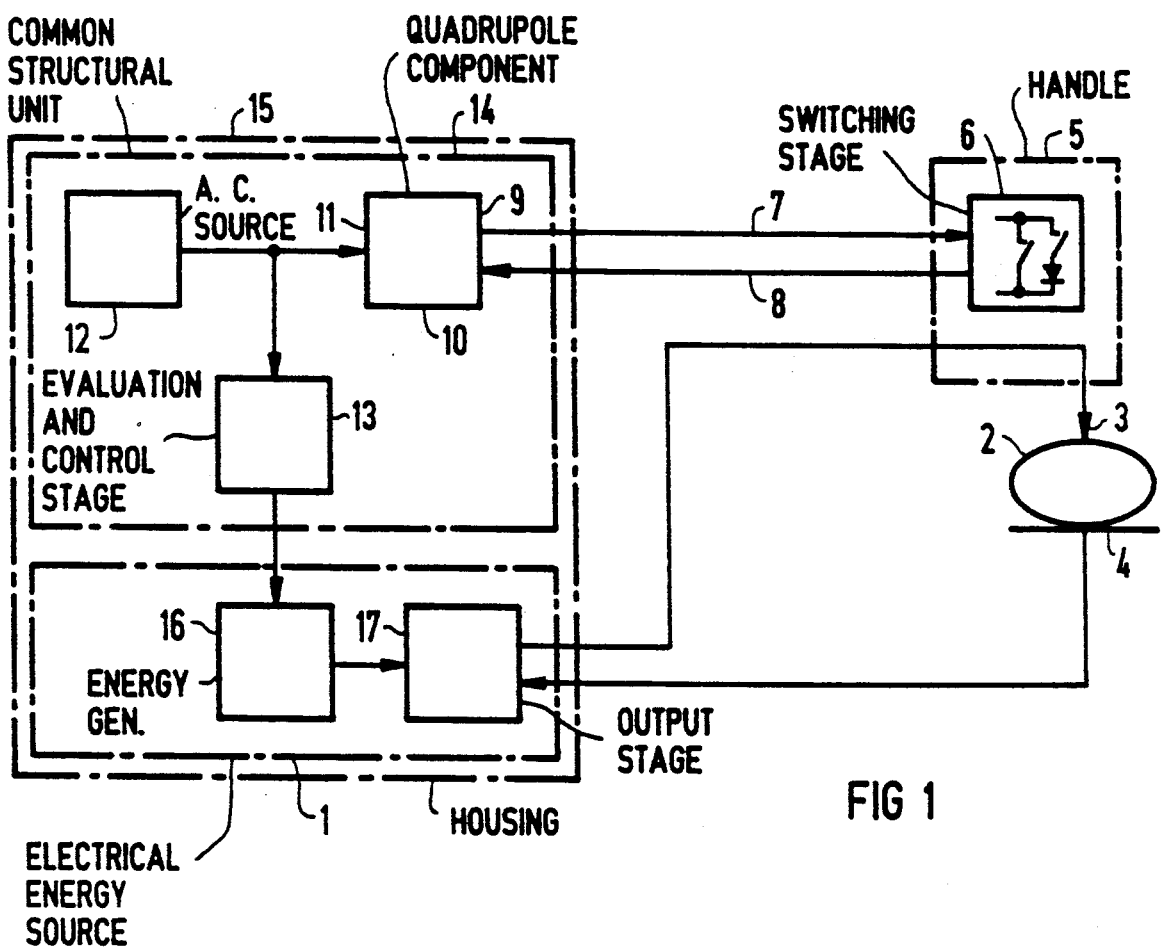
FIG. 1 is a simplified block diagram of an electro-therapy device constructed in accordance with the principles of the present invention.

FIG. 1 is a general block diagram of an electro-therapy device constructed in accordance with the principles of the present invention. The device may be any type of apparatus for administering treatment to a patient in the form of electrical energy. The electrical energy which is administered to the patient may be energy for conducting electro-surgery, for stimulating an organ, or any other medical purpose.

The device of FIG. 1 therefore includes an electrical energy source 1. The energy is supplied to a patient 2 via electrodes 3 and 4, with at least one electrode 3 carrying a high voltage, the voltage at the electrode 3 being "high" with reference to the other electrode 4 and/or ground. The electrode 3 is held and manipulated by a handle 5, which also includes a switching stage 6. The switching stage 6 includes at least one switch connected in series with a rectifier. The switching stage 6 is electrically connected via lines 7 and 8 to the secondary side 9 of a quadrupole component 10, which transmits alternating current and blocks direct current. The primary side 11 of the quadrupole 10 is coupled to an alternating current source 12, and to an evaluation and control stage 13. Actuation of at least one switch within the switching stage 6 causes a directionally dependent reaction at the primary side 11 of the quadrupole component 10. This directionally dependent reaction is detected and evaluated by the evaluation and control stage 13. The evaluation and control stage 13 is connected to an energy generator 16 within the therapeutic electrical energy source. The energy generator 16 delivers electrical energy to the patient 2 via an output stage 17. When the evaluation and control stage 13 detects a directionally dependent reaction at the primary side 11 of the quadrupole component 10, it supplies a signal to the energy generator 16, which causes the energy delivered to the patient 2 to be appropriately altered.

If, for example, a switch within the switching stage 6 is closed, this causes a short circuit to be present at the secondary side of the quadrupole component 10. This short circuit causes a reaction at the primary side 11 resulting, among other things in a change in the current at the primary side, to which the evaluation and control stage 13 can respond and trigger a control function in the therapeutic electrical energy source 1 which is designated to occur when such a change of current is detected. The alteration in the electrical energy delivered to the patient may be, for example, to switch the maximum power on.

If, as a further example, a switch connected in series with a diode within the switching stage 6, for example a push button, is closed, a short circuit will be present at the secondary side 9 of the quadrupole component 10 for only one direction of current flow. This causes a different directionally dependent reaction at the primary side 11 by producing, among other things, a change in current at the primary side 11 in only one direction (the effective current will thus be lower than in the first example). This is detected and evaluated by the evaluation in control stage 13 (for example, via low-voltage opto-couplers) which triggers a different control function in the therapeutic electrical energy source 1 so that an alteration in the electrical energy delivered to the patient 2, which is a different alteration than was undertaken in the first example, occurs. This different alteration may be, for example, a reduction in the power of the electrical energy delivered to the patient.

As also shown in FIG. 1, the quadrupole component 10, the a.c. source 12 and the evaluation and control stage 13 are all disposed on a common structural unit 14. The structural unit 14 and the therapeutic electrical source 1 are contained in a common housing 15. The housing 15 is equipped with terminals (not shown) for the electrodes 3 and 4 and for the lines 7 and 8.

Figure 2:
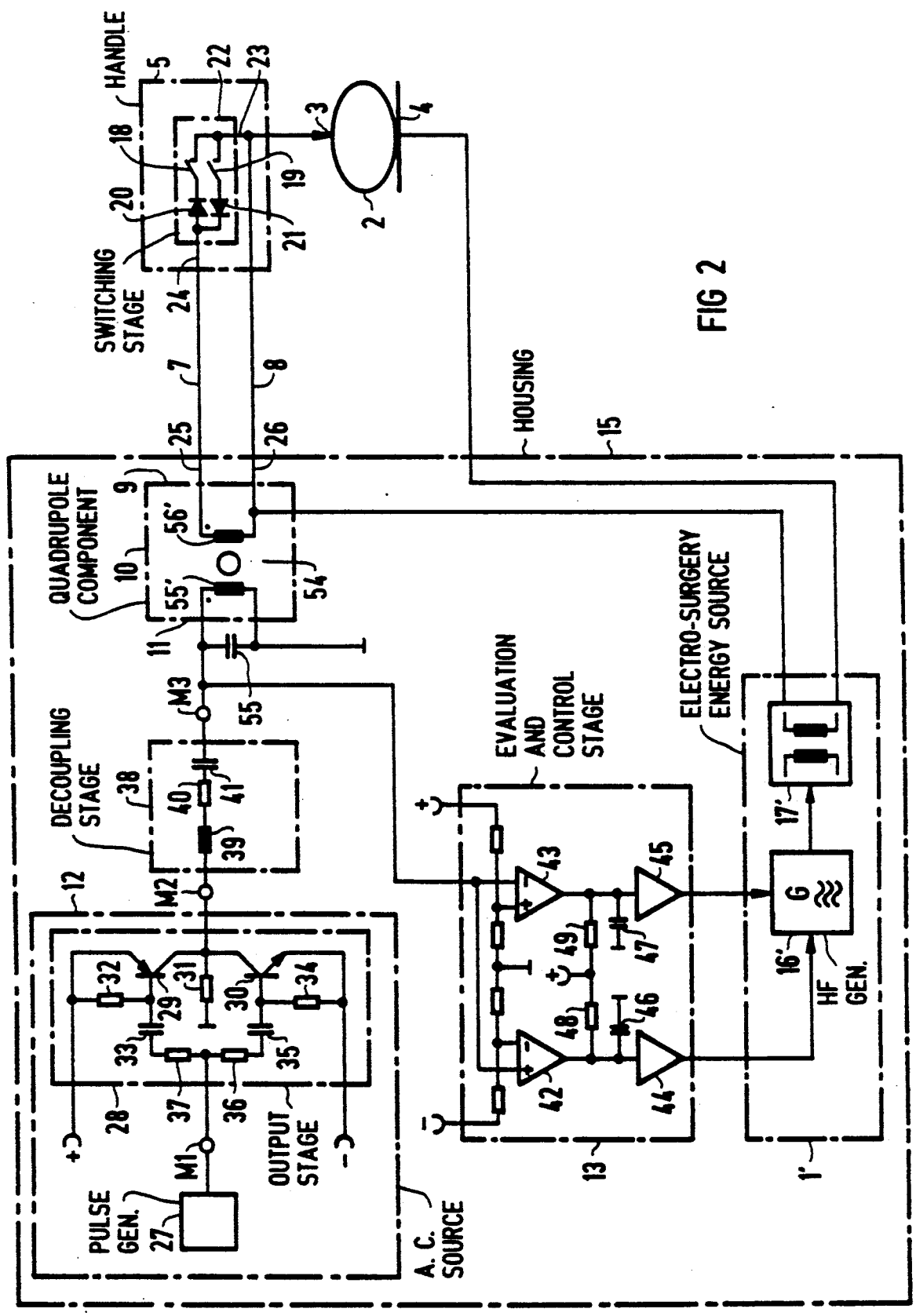
FIG. 2 is a simplified block diagram of an embodiment of a high frequency surgery device constructed in accordance with the principles of the present invention.

As noted above, the device shown in FIG. 1 is a generalized representation of any type of device for administering electrical energy to a patient for medical purposes. An example of such a device is a high-frequency surgery device, and such a device is shown in FIG. 2, which embodies the arrangement of components shown in FIG. 1. Therefore in the embodiment of FIG. 2, the quadrupole component 10, the a.c. source 12 and the evaluation and control stage 13 and an electro-surgery energy source 1' are all contained in a housing 15 (as well as a decoupling stage 38 described below).

The electro-surgery energy source 1' includes a high-frequency generator 16' as the energy generator, and a transformer 17' as the output stage.

The housing 15 is remote from a handle 5 and is connected thereto via lines 7 and 8. The electrical energy from the electro-surgery energy source 1 is also transmitted to the electrode 3 via the line 8, therefore the handle 5 is relieved of one line and is consequently easier to manipulate.

The switching stage in the handle 5 includes switches 18 and 19 respectively connected in series with diodes 20 and 21. These series combinations are connected in parallel with the diodes connected with opposite polarity. The switching stage thus constitutes a two-port network 22, which is connected in voltaically conductive fashion to the electrode 3 (or the line 8) leading to the electro-surgery energy source 1'. The other port 24 of the network 22 is voltaically connected to the line 7 leading to the housing 15 and connected to the secondary side of the quadrupole component 10 at a terminal 25. A second terminal 26 of the secondary side of the quadrupole component 10 is voltaically connected to the line 8 which leads to the electrode 3. The diodes 20 and 21 thus also result in the elimination of transmission lines. The diodes 20 and 21 may alternatively be disposed in the housing 15 at the secondary side of the quadrupole component 10. If this is done, a conventional electrode handle may be fitted with an additional line, so that existing electrode handles are compatible with the circuit arrangement disclosed herein. To protect the diodes, or to reduce the load at the quadrupole component 10, an ohmic resistor (not shown) can be inserted.

In the embodiment of FIG. 2, the a.c. current source 12 is in the form of a pulse generator circuit having an output stage 28 formed by a series circuit of complementary transistors 29 and 30 whose collectors are connected to ground via a common load resistor. One emitter is connected to a positive voltage source and the other emitter is connected to a negative voltage source. A resistor 32 and a capacitor 33 form a RC element at the base of transistor 29, and a resistor 34 and a capacitor 35 form an RC element at the base of the transistor 30. The transistors 29 and 30, which may be field effect transistors, thus function as respective monostable trigger circuits which are switched in alternation by pulses having positive and negative leading edges. The pulses are supplied to the respective bases of the transistors 29 and 30 from a pulse generator 27 via respective resistors 37 and 36. The average power consumption can thus be reduced in comparison to an alternating current source having continuous alternating current, which contributes to reducing the insulation necessary at the quadrupole component 10.

Figure 6:
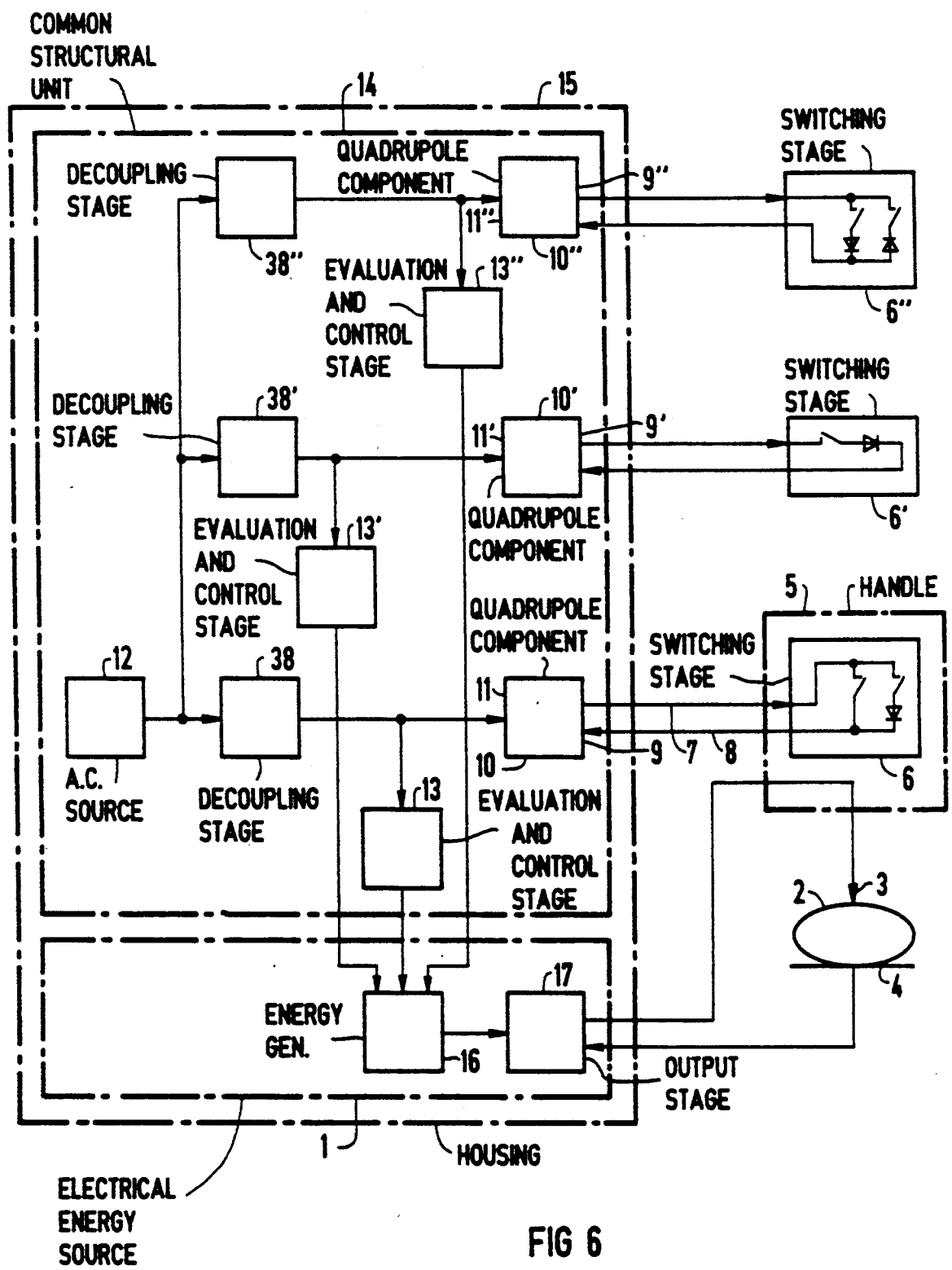
FIG. 6 is a block diagram of a further embodiment of the device of FIG. 2 with multiple quadrupole components.

The output of the a.c. source 12 (i.e., the output of the output stage 28) is coupled to the primary side 11 of the quadrupole component 10 via a decoupling stage 38. The decoupling stage 38 consists of a coil 39, a resistor 40 and a capacitor 41. The decoupling stage 38 permits reactions at the primary side 11 of the quadrupole component 10 which proceed from the switching stage to be better interpreted by the evaluation and control stage 13. Additionally, as shown in FIG. 6, further quadrupole components (having respectively different potentials at the secondary side) can be connected to the output stage 28 of the a.c. source 12 via further decoupling means. (In FIG. 6, the additional quadrupole components and associated function blocks are identified in sets numbered respectively with primes and doubleprimes.) This permits additional switches to be provided which can trigger further functions, for example alarm and/or monitoring functions, at the same time or at a different electrode. For example, the coil 39 may function as a part of a decoupling means shared by a plurality of quadrupoles, with respective resistors and/or capacitors associated with further quadrupole components functioning as the remainder of the separate decoupling means for each of those quadrupole components.

Figure 4:
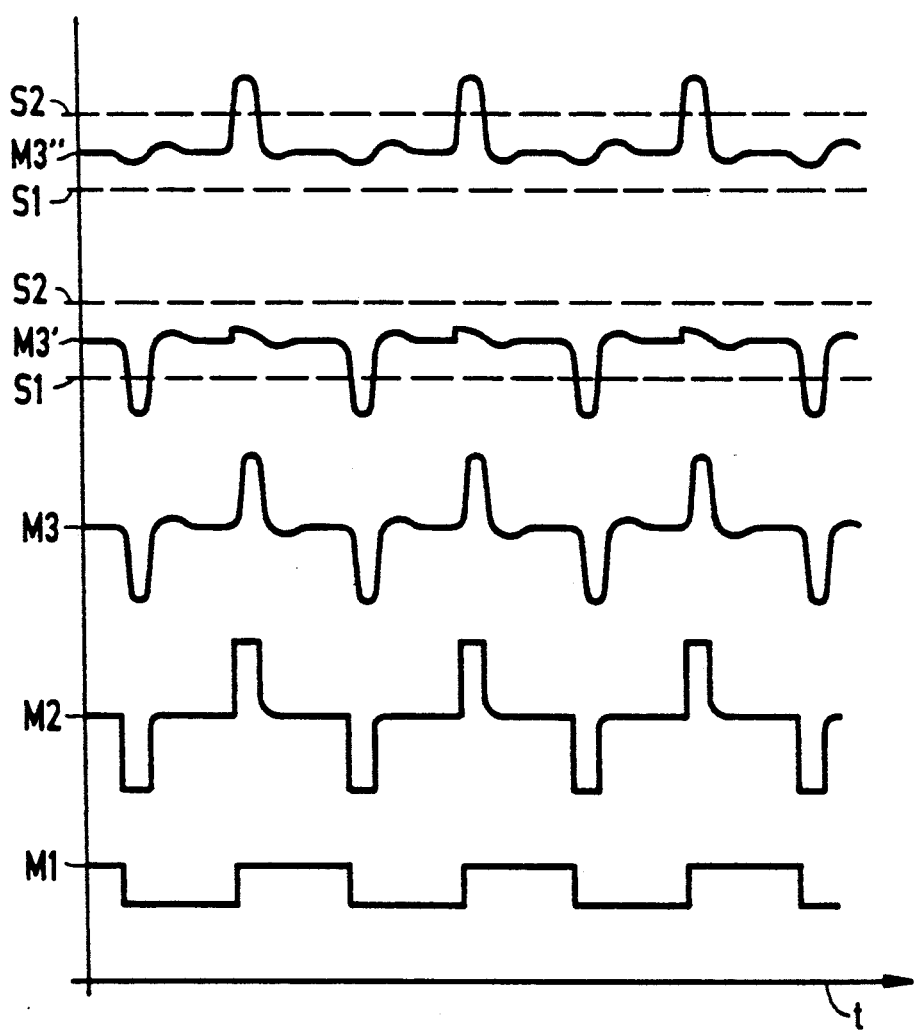
FIG. 4 is a pulse diagram for explaining the operation of the device shown in FIG. 2.

The evaluation and control stage 13 includes two comparators 42 and 43 having a respective non-inverting input and an inverting input connected to the primary side 11 of the quadrupole component 10, and functioning as the inputs for the evaluation and control stage 13. A negative voltage is present at the inverting input of the comparator 42, and a positive voltage is present at the non-inverting input of the comparator 43. The output of the comparator 42 is supplied as an input to a gate module 44, and the output of the comparator 43 is supplied as an input to a logic module 45. The comparator 42 maintains the logic input of the module 44 inhibited given transgression of a positive threshold voltage S2 (see FIG. 4). The comparator 43 maintains a logic input of the module 45 inhibited given a transgression of a negative threshold voltage S1. Charging capacitors 46 and 47 are charged positively over time via respective resistors 48 and 49. As long as pulses are present at the comparator inputs which exceed the prescribed threshold voltage S1 or S2 in terms of magnitude, the comparators result in the discharge of the capacitors 46 and 47. The gate modules 44 and 45 therefore do not trigger any function at the high-frequency generator 16'. If one of the switches 18 or 19 is closed, substantially a short circuit exists for one direction of current flow at the secondary side 9 of the quadrupole component 10. This modifies the pulses at the primary side 11 which are supplied to the comparator inputs, as the two upper pulse curves in FIG. 4 show, and as is described in further detail below. As a result, the capacitor 46 or 47 is no longer discharged, and the gate module 44 or 45, after adequate charging of the capacitor 46 or 47, triggers the function allocated thereto at the high-frequency generator 16' (i.e., at the electro-surgery energy source 1'). If both switches 18 and 19 are actuated, both functions which are allocated to the comparators 44 and 45 are triggered at the high-frequency generator 16'. In order to prevent the gate modules 44 and 45 from triggering their respective functions in the event of an outage of the a.c. source 12, a positive voltage, for safety reasons, can be supplied to the resistors 48 and 49 via a gate circuit (not shown) which is open when an alternating current signal is present at the output of the a.c. source 12.

Figure 3:
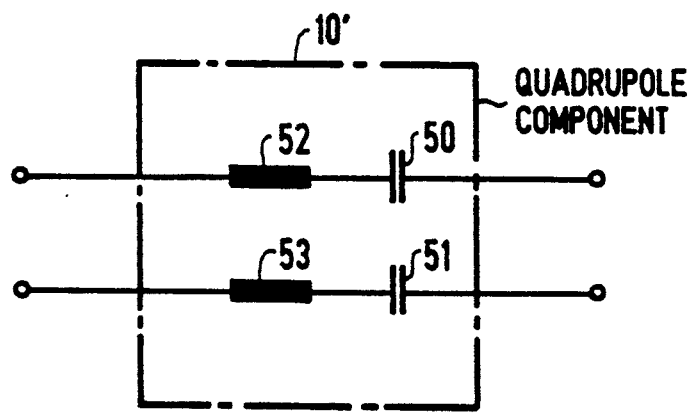
FIG. 3 is a circuit diagram of a quadrupole component of the type suitable for use in the devices of FIGS. 1 and 2.

The quadrupole component 10 can be designed mechanically and/or electrically in a number of different ways. If only high d.c. voltages are expected to be present at the electrode 3, a quadrupole component 10 which contains two capacitors suffices. In FIG. 3, an embodiment is shown wherein respective coils 52 and 53 are connected in series with two capacitors 50 and 51. This quadrupole component 10' can be used in high-frequency surgery devices, particularly if the respective series resonant circuits consisting of the capacitor 50 and the coil 52, and the capacitor 51 and the coil 53, are tuned to the frequency (for example, 4 kHz) of the a.c. source 12. The quadrupole component 10' functions as a blocking filter for the high frequency of, for example, 500 kHz.

The combination of the switches 18 and 19 can assume four different states, with each state being conveyed via the quadrupole component 10 to the evaluation and control stage 13 so that the output of the electro-surgery energy source 1' (i.e., the electrical energy delivered to the patient 2) can be altered in four ways. If the switches 18 and 19 are open, this can constitute the "off" condition, and the switches can assume the further states of only switch 18 being closed, only switch 19 being closed, or both switches 18 and 19 being closed. The four different alterations in the energy delivery are thus achieved while using only one quadrupole component 10, and therefore only the quadrupole component 10, and the connecting sockets at the housing 15, need be adequately insulated.

As noted above, FIG. 4 shows a pulse diagram for the signals at various locations in the circuit of FIG. 2 with time being entered on the horizontal axis. The bottom curve shows square-wave pulses of the type which are present at the measuring location M1 at the output of the pulse generator 27 in FIG. 2. The curve which is shown second from the bottom in FIG. 4 is present at the output circuit 28 at the measuring point M2. The pulse duration is short in comparison to the spacing to the next pulse. This provides sufficient time for the execution of the aforementioned charging events. The pulse durations of the positive and negative pulses are of the same size, and the positive and negative pulse voltages have the same magnitude. As a result, the threshold voltages S1 and S2, shown in the upper two curves of FIG. 4, at the comparators 42 and 43 can be realized in a simple way, and the discharging events at the capacitors 46 and 47 can be controlled with little outlay. The third curve from the bottom in FIG. 4 shows the pulse signal at the measuring point M3. The rounding-off and overshoots arise due to the decoupling stage 38 in combination with a capacitor 55, which is primarily to short to ground any remaining high frequency energy at the primary side of the quadrupole component 10.

The two upper curves M3' and M3" respectively represent signals at the measuring point M3 when the switch 19 is closed (M3') and when the switch 18 is closed (M3"). The dashed lines represent the threshold voltages S1 and S2 at the respective comparators 42 and 43. The voltages S1 and S2 are respectively set to enable reliable switching due to the incoming pulses which can be expected based on the alternating current signal (which may, in other embodiments, differ from those shown in FIG. 4).

Figure 5:
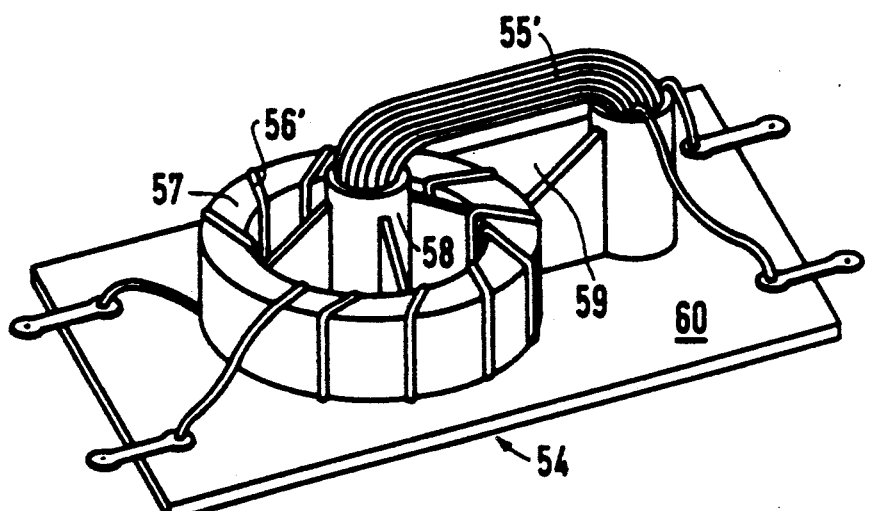
FIG. 5 is a perspective view of an embodiment of the quadrupole component suitable for use in the devices of FIGS. 1 and 2 in the form of a toroidal core pulse transformer.

An exemplary structural arrangement for the quadrupole component 10 is shown in FIG. 5. In FIG. 5, the quadrupole component 10 is in the form of a toroidal core pulse transformer. The component of FIG. 5 has the electrical diagram shown in FIG. 2. The primary winding 55' and the secondary winding 56' of the toroidal core pulse transformer 54 can be arranged on the toroidal core 57 at a large distance from one another with a low capacitance relative to each other. This results in an economic and reliable separation of potentials with low coupling capacitance of the windings 55' and 56', even given high-frequency peak voltages which may extend up to 10 kV. For example, the secondary winding 56' may be wound tightly adjacent to and distributed over substantially the entire surface of the toroidal core, and the primary winding 55' can be wound roughly in a rectangular shape similar to a flat coil, with one section of the winding 55' proceeding through a center 58 of the toroidal core 57, and a section of the toroidal core 57 proceeding substantially through a center 59 of the winding 55'. The toroidal core 57 and the winding 55' can thus be held orthogonally by a one-piece plastic holder 60, with the insulation between the windings 55' and 56' being formed substantially by the large distances between the windings 55' and 56', thereby minimizing the necessity of further insulating steps. Moreover, the plastic holder 60 can be fashioned so that long creep paths will result for stray currents between the windings.

Although modifications and changes may be suggested by those skilled in the art, it is the intention of the inventor to embody within the patent warranted hereon all changes and modifications as reasonably and properly come within the scope of this contribution to the art.

I claim as my invention:

1. An apparatus for administering treatment to a patient in the form of electrical energy, said apparatus comprising:

a source of electro-surgery energy;

electrode means connected to said source of electro-surgery energy and adapted for delivering said electro-surgery energy to a patient;

an a.c. source;

quadrupole means, connected to said a.c. source, for transmitting alternating current and blocking direct current, said quadrupole means having a primary side connected to said a.c. source and a secondary side voltaically separated from said primary side;

switch means, including a series connected rectifier and user-actuatable switch forming a series branch bridging said secondary side of said quadrupole means, for causing a directionally-dependent change in an electrical parameter at said primary side of said quadrupole means upon actuation of said switch means; and evaluation and control means connected to said primary side of said quadrupole means and to said a.c. source for detecting said directionally dependent change and for altering delivery of said electro-surgery energy to said patient via said electrode means in response to said directionally-dependent change.

2. An apparatus as claimed in claim 1 wherein said evaluation and control means includes means for detecting a change in the direction of current flow in said primary side of said quadrupole means.

3. An apparatus as claimed in claim 1 wherein said evaluation and control means includes means for detecting a change in voltage polarity at said primary side of said quadrupole means.

4. An apparatus as claimed in claim 1 wherein said switch means further includes a further user-actuatable switch and a further rectifier connected in series forming a further series branch, said series branch and said further series branch being connected in parallel, with said rectifier and said further rectifier having opposite polarity, and forming a two-port network connected across said secondary side of said quadrupole means.

5. An apparatus as claimed in claim 4 wherein said rectifier and said further rectifier and said electrode means are disposed in a first structural component and wherein said quadrupole means, said a.c. source, said source of electro-surgery energy and said evaluation and control means are disposed in a second structural component remote from said first structural component.

6. An apparatus as claimed in claim 4 wherein one port of said two-port network and one terminal of the secondary side of said quadrupole means are electrically connected to said electrode means.

7. An apparatus as claimed in claim 4 wherein said evaluation and control means comprises:
- a first comparator having a non-inverting input connected to said primary side of said quadrupole means and having a positive threshold;
- a second comparator having an inverting input connected to said primary side of said quadrupole means and having a negative threshold;
- said a.c. source causing a normal pattern of transgression of said positive and negative thresholds, and actuation of said switch causing an alteration in the transgression pattern for said positive threshold and thereby changing the output of said first comparator and actuation of said further switch causing an alteration in the transgression pattern of said negative threshold and thereby causing a change in the output of said second comparator; and
- means connected to said first and second comparators and responsive to changes in the outputs of said first and second comparators for generating control signals to said source of electro-surgery energy for altering delivery of said electro-surgery energy to said patient.

8. An apparatus as claimed in claim 7 wherein said means for generating control signals comprises:
- a first logic module and a first charging capacitor connected to the output of said first comparator, said first logic module having an input which is inhibited by a transgression of said positive threshold; and
- a second logic module and a second charging capacitor connected to the output of said second comparator, said second logic module having an input which is inhibited by a transgression of said negative threshold.

9. An apparatus as claimed in claim 7 wherein said evaluation and control means further comprises means for preventing an alteration in the delivery of said electro-surgery energy to said patient in the event of an outage of said a.c. source.

10. An apparatus as claimed in claim 1 wherein said evaluation and control means includes means for detecting changes in power consumption at said primary side of said quadrupole means caused by said directionally dependent change.

11. An apparatus as claimed in claim 1 further comprising a decoupling stage connected between said a.c. source and said primary side of said quadrupole means.

12. An apparatus as claimed in claim 1 wherein said quadrupole means is a toroidal core pulse transformer and wherein said a.c. source is a pulse generator means for generating output pulses having alternating polarity to a primary winding of said transformer which forms the primary side of said quadrupole means, and said transformer having a secondary winding connected to said switch means forming said secondary side of said quadrupole means.

13. An apparatus as claimed in claim 12 wherein said pulse generator means includes an output stage comprising first and second complementary transistors having respective collectors connected to each other and connected to ground via a common load resistor, one transistor having an emitter adapted for connection to a positive voltage source and the other transistor having an emitter adapted for connection to a negative voltage source, a first RC element connected to the base of said first transistor and a second RC element connected to the base of said second transistor, said first and second RC elements being supplied with said pulses of alternating polarity so that each transistor functions as a monostable trigger circuit with the monostable circuits being switched in alternation by said pulses.

14. An apparatus as claimed in claim 12 wherein said pulse generator means is a means for generating pulses having a pulse duration which is short in comparison with the pulse-to-pulse spacing.

15. An apparatus as claimed in claim 12 wherein said pulse generator means is a means for alternating positive and negative pulses having substantially the same magnitude and duration.

16. An apparatus as claimed in claim 1 wherein said quadrupole means is a toroidal core pulse transformer having a primary winding and a secondary winding with said primary and secondary windings being insulated from each other primarily by a distance therebetween, and wherein said primary and secondary windings have a low capacitance relative to each other.

17. An apparatus as claimed in claim 1 wherein said quadrupole means is a toroidal core pulse transformer having first and second windings, one of said windings being wound tightly around and evenly distributed over substantially the entire surface of a toroidal core, and the other winding being wound in a substantially rectangular shape and having one section proceeding through a center of said toroidal core, and said toroidal core having a section proceeding substantially through a center of said rectangle.

18. An apparatus as claimed in claim 17 wherein said quadrupole means further comprises a holder for said toroidal core and said rectangular winding which holds said toroidal core and said rectangular winding orthogonally relative to each other.

19. An apparatus as claimed in claim 18 wherein said holder is a one-piece plastic component.

20. An apparatus as claimed in claim 18 wherein said winding on said toroidal core is a secondary winding for said transformer forming said secondary side of said quadrupole means and wherein said rectangular winding is a primary winding for said transformer forming said primary side of said quadrupole means.

21. An apparatus as claimed in claim 1 further comprising a further user-actuatable switch connected in parallel with said series branch bridging said secondary side of said quadrupole means.

* * * * *